US010093698B2

(12) United States Patent
Chung et al.

(10) Patent No.: US 10,093,698 B2
(45) Date of Patent: Oct. 9, 2018

(54) PEPTIDE HAVING EFFICACY FOR REMEDYING HYPOPIGMENTATION AND INHIBITING ADIPOGENESIS, AND USE OF SAME

(71) Applicant: CAREGEN CO., LTD., Anyang-si (KR)

(72) Inventors: Yong Ji Chung, Yongin-si (KR); Eun Mi Kim, Yongin-si (KR); Eung Ji Lee, Anyang-si (KR); Kyoung Mi Cho, Cheonan-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 15/307,587

(22) PCT Filed: Nov. 21, 2014

(86) PCT No.: PCT/KR2014/011273
§ 371 (c)(1),
(2) Date: Oct. 28, 2016

(87) PCT Pub. No.: WO2015/174599
PCT Pub. Date: Nov. 19, 2015

(65) Prior Publication Data
US 2017/0051014 A1     Feb. 23, 2017

(30) Foreign Application Priority Data

May 13, 2014   (KR) .................. 10-2014-0057189

(51) Int. Cl.
*A61K 38/08*   (2006.01)
*A61K 38/00*   (2006.01)
*C07K 7/06*    (2006.01)

(52) U.S. Cl.
CPC .............. *C07K 7/06* (2013.01); *A61K 38/08* (2013.01); *A61K 38/00* (2013.01)

(58) Field of Classification Search
CPC .......... A61K 38/00; A61K 38/08; C07K 7/06
USPC .......................... 514/21.6, 1.1; 530/328, 300
See application file for complete search history.

(56) References Cited

U.S. PATENT DOCUMENTS

| 6,303,749 B1 | 10/2001 | Jarosinski |
| 8,058,240 B2 * | 11/2011 | Haskell-Luevano ........ C07K 14/47 514/10.7 |
| 2011/0217414 A1 | 9/2011 | Schnorr et al. |
| 2012/0244575 A1 * | 9/2012 | Poth ...................... C07K 14/415 435/68.1 |

FOREIGN PATENT DOCUMENTS

| JP | H08503693 A | 4/1996 |
| JP | 2002-501012 A | 1/2002 |
| JP | 2005-531496 A | 10/2005 |
| JP | 2007-077119 A | 3/2007 |
| JP | 2007-537976 A | 12/2007 |
| JP | 2010-535758 A | 11/2010 |
| KR | 10-0889460 B1 | 3/2009 |
| KR | 20110130282 A | 12/2011 |

OTHER PUBLICATIONS

Chal et al., "Inverse agonist activity of agouti and agouti-related protein," Peptides. 24(4):603-9 (2003).
Mundy et al., "Investigation of the role of the agouti signaling protein gene (ASIP) in coat color evolution in primates," Mamm Genome. 17(12):1205-13 (2006).
Office Action dated Oct. 3, 2017 for Japanese Patent Application No. 2016-565255, Tanaka et al., "Peptide Having Efficacy for Remedying Hypopigmentation and Inhibiting Adipogenesis and Use of Same," filed Nov. 21, 2014 (11 pages).
Rieder et al., "Mutations in the agouti (ASIP), the extension (MC1R), and the brown (TYRP1) loci and their association to coat color phenotypes in horses (*Equus caballus*)," Mamm Genome. 12(6):450-5 (2001).
International Search Report for International Application No. PCT/KR2014/011273, dated Feb. 23, 2016 (8 pages).
Kim, Soon Jin, "AP1 inhibits adipogenesis through down-regulation of PPAR$_{gamma}$ and modulation of PI3K/akt and FoxO pathways in 3T3-L1 cells," Master of Science, Graduate Department of Microbiology, Pukyong National University, Feb. 2013 (17 pages).
Kobayashi et al., "Tyrosinase related protein 1 (TRP1) functions as a DHICA oxidase in melanin biosynthesis," EMBO J. 13(24):5818-25 (1994).
Marshall, "Specificity of receptor tyrosine kinase signaling: transient versus sustained extracellular signal-regulated kinase activation," Cell. 80(2):179-85 (1995).
Sori et al., "Hypopigmentary disorders in children in South India," Indian Journal of Dermatology. 56(5): 546-9 (5 pages) (2011).
Voisey et al., "Agouti: from mouse to man, from skin to fat," Pigment Cell Res. 15(1):10-8 (2002).
Extended European Search Report dated Nov. 29, 2017 for European Patent Application No. 14891893.1, Chung et al., "Peptide having efficacy for remedying hypopigmentation and inhibiting adipogenesis, and use of same," filed Nov. 21, 2014 (10 pages).

(Continued)

*Primary Examiner* — Julie Ha
(74) *Attorney, Agent, or Firm* — Clark & Elbing LLP; Susan M. Michaud

(57) ABSTRACT

A peptide formed from the amino acid sequence of SEQ ID NO: 1 or SEQ ID NO: 2 shows a melanogenesis increment activity and an adipogenesis inhibitory activity. The peptide, by increasing phosphorylation of MITF, which is a transcription factor for increasing a tyrosinase expression, and CREB for increasing an MITF expression, consequently increases a tyrosinase expression and ultimately increases melanin synthesis. The peptide, by reducing the amount of fat accumulated inside a cell and reducing expressions of perilipin and PPARγ, which contribute to adipogenic mechanism, ultimately inhibits adipogenesis. A composition for remedying or treating melanin hypopigmentation, a composition comprising the peptide, and a pharmaceutical composition for treating or preventing obesity, are provided.

11 Claims, 12 Drawing Sheets

Specification includes a Sequence Listing.

(56) References Cited

OTHER PUBLICATIONS

Joseph et al., "Chimeric NDP-MSH and MTII melanocortin peptides with agouti-related protein (AGRP) Arg-Phe-Phe amino acids possess agonist melanocortin receptor activity," Peptides. 24(12):1899-908 (2003).

Millhauser et al., "Loops and links: structural insights into the remarkable function of the agouti-related protein," Ann N Y Acad Sci. 994:27-35 (2003).

Schentrup, Anzeela, thesis: "Structure-activity relationships of an agouti-related protein-derived decapeptide at the murine melanocortin receptors," Master of Science, University of Florida, 2005 (43 pages).

Suzuki et al., "Agouti signaling protein inhibits melanogenesis and the response of human melanocytes to alpha-melanotropin," J Invest Dermatol. 108(6):838-42 (1997).

Wilczynski et al., "Current trends in the structure-activity relationship studies of the endogenous agouti-related protein (AGRP) melanocortin receptor antagonist," Med Res Rev. 25(5):545-56 (2005).

\* cited by examiner

PEPTIDE HAVING EFFICACY FOR REMEDYING HYPOPIGMENTATION AND INHIBITING ADIPOGENESIS, AND USE OF SAME

TECHNICAL FIELD

This application claims priority to and the benefit of Korean Patent Application No. 10-2014-0057189 filed in the Korean Intellectual Property Office on 13 May 2014, the entire contents of which are incorporated herein by reference.

The present invention relates to a peptide having hypomelanosis alleviating and adipogenesis inhibitory efficacies and a use thereof.

BACKGROUND ART

Melanin is produced by tyrosinase from tyrosine via DOPA in melanocytes, which are pigmentation cells present in the stratum basale in the epidermis, and it has been known that tyrosinase-related protein-1/2 (Trp-1/2), in addition to tyrosinase, is involved in the melanin biosynthesis procedure (Korner and Pawelek, Science (1982) 217:1163-1165; Kobayashi et al., EMBO J (1994) 13:5818-5825; and Yokoyama et al., Biochim Biophys Acta (1994) 1217:317-321), and cyclic AMP (cAMP) and extracellular signal-activated kinases-1/2 (ERK1/2) thereby are continuously involved as upper signals of tyrosinase expression (Marshall, Cell (1995) 80:179-185; and Busca and Ballotti, Pigment Cell (2000) 13:60-69).

Melanocytes are affected by several factors, such as external conditions (e.g., ultraviolet radiation and inflammation) and hormones (e.g., melanin stimulating hormone (MSH) and thyroid stimulating hormone (TSH)).

Melanin absorbs the light energy of ultraviolet light in the sunlight to protect cells that are deep in the skin from damage due to the ultraviolet light, but the abnormal excessive production of melanin causes abnormal skin pigmentation, such as chloasma, freckles, or pigmentation, and on the contrary, the less production of melanin causes hypomelanosis (leukoderma), such as vitiligo, nevus depigmentosus, pseudoleucoderma atopicum, Tinea versicolor, morphea, allergy, post-inflammatory depigmentation, idiopathic guttate hypomelanosis, and piebaldism (Bolognia and Pawelek, J Am Acad Dermatol (1988) 19:217-255; and Pinto and Bolognia, Pediatr Clin North Am (1991) 38:991-1017).

Of the hypomelanosis diseases, vitiligo results from the destruction of melanocytes, and the other diseases result from a reduction in the amount of melanin produced in melanocytes.

For the treatment of the above diseases, there are photochemical methods using light sensitizers such as psoralen, invasive methods such as surgery, and methods inducing skin re-pigmentation through the administration of drugs having melanocyte proliferation activity or melanogenesis promotion activity, such as the ingredients of leadwort root, ginger, pippali, and black pepper (Ancient Science of Life, (1990) Vol. IV, No. 4, 202-206).

Obesity, which is the cause of various diseases, is responsible for 80% of diabetic patients and 21% of heart disease patients, and causes huge social and economical losses. Therefore, the development of safe and effective anti-obesity drugs can reduce the huge social and economical losses. However, the medicines capable of solving market situations are limited to appetite suppressants and fat uptake inhibitors, falling short of expectations, and have various side effects as described below. Xenical (Roche) induced the inhibition of lipase secreted from the pancreas and the digestive system to inhibit fat absorption, accompanied by side effects, such as a low weight loss effect of 2-3% and frequent diarrhea. Reductil (Abbott) suppresses the appetite through the inhibition of serotonin and noradrenaline uptake, leading to a weight loss effect of 5-10%, but has side effects including cardiovascular diseases, such as stroke and myocardial infarction, so Reductil was removed from the market by the European Medicines Agency (EMA) and the US Food and Drug Administration (FDA) in 2010 through the suspension of use and prescription and the recommendations for voluntary recall, and was taken off the market by Korea Food & Drug Administration on October 2010. Further, a large number of products that have been developed as an anti-obesity drugs have so far been prohibited from being sold due to severe side effects thereof. For example, aminophylline has been reported to have broad side effects throughout the mental nervous system, circulatory system, and digestive system in spite of its excellent effect of reducing body fat. Also, fenfluramine, dexfenfluramine, topiramate, ephedrine, etc. have been banned from being marketed as obesity drugs.

Throughout the entire specification, many papers and patent documents are referenced and their citations are represented. The disclosure of the cited papers and patent documents are entirely incorporated by reference into the present specification and the level of the technical field within which the present invention falls, and the details of the present invention are explained more clearly.

DETAILED DESCRIPTION OF THE INVENTION

Technical Problem

The present inventors endeavored to develop excellent peptides having biologically effective activity, and as a result, the present inventors established that a peptide having the amino acid sequence of SEQ ID NO: 1 or 2 has excellent physiological activity, such as increasing melanogenesis and inhibiting adipogenesis, and thus the present inventors completed the present invention.

Therefore, an aspect of the present invention is to provide a peptide having melanogenesis increasing or adipogenesis inhibitory activity.

Another aspect of the present invention is to provide a composition for alleviating or treating hypomelanosis.

Still another aspect of the present invention is to provide a pharmaceutical composition for treating or preventing obesity.

Other purposes and advantages of the present disclosure will become more obvious with the following detailed description of the invention, claims, and drawings.

Technical Solution

According to an aspect of the present invention, the present invention provides a peptide having a melanogenesis increasing activity and including one amino acid sequence selected from the group consisting of amino acid sequences of SEQ ID NO: 1 and SEQ ID NO: 2.

According to another aspect of the present invention, the present invention provides a peptide having an adipogenesis inhibitory activity and including one amino acid sequence selected from the group consisting of amino acid sequences of SEQ ID NO: 1 and SEQ ID NO: 2.

The present inventors endeavored to develop excellent peptides having biologically effective activity, and as a result, the present inventors established that a peptide having the amino acid sequence of SEQ ID NO: 1 or 2 has excellent physiological activity, such as increasing melanogenesis and inhibiting adipogenesis.

The peptide of the present invention includes the amino acid sequence of SEQ ID NO: 1 or SEQ ID NO: 2. Specifically, the peptide of the present invention essentially includes the amino acid sequence of SEQ ID NO: 1 or SEQ ID NO: 2.

According to one embodiment of the present invention, the peptide of SEQ ID NO: 1 or SEQ ID NO: 2 exhibits activity to increase melanogenesis and inhibit adipogenesis.

According to another embodiment of the present invention, the peptide of the present invention increases the phosphorylation of microphthalmia-associated transcription factor (MITF), which is a transcription factor to increase the expression of a melanogenic enzyme (tyrosinase), and cAMP-responsive element binding protein (CREB), which increases the expression of MITF, thereby resultantly increasing the expression of tyrosinase, and ultimately increasing melanogenesis.

According to another embodiment of the present invention, the peptide of the present invention reduces the amount of fat accumulated in cells and reduces the expressions of perilipin and peroxisome proliferator-activated receptor gamma (PPARγ) involved in the adipogenesis mechanism, thereby ultimately inhibiting adipogenesis.

As used herein, the term "peptide" refers to a linear molecule in which amino acid residues bind to each other via a peptide linkage. The peptide of the present invention may be prepared by a chemical synthesis method, especially solid-phase synthetic techniques (Merrifield, J. Amer. Chem. Soc. 85:2149-54(1963); Stewart, et al., Solid Phase Peptide Synthesis, 2nd. ed., Pierce Chem. Co.: Rockford, 111(1984)) or liquid-phase synthetic techniques (U.S. Pat. No. 5,516, 891).

According to an embodiment of the present invention, a protecting group, which is selected from the group consisting of an acetyl group, a fluorenyl methoxy carbonyl group, a formyl group, a palmitoyl group, a myristyl group, a stearyl group, and polyethylene glycol (PEG), may be linked to the N- or C-terminus of the peptide.

The foregoing amino acid modification significantly improves the stability of the peptide of the present invention. As used herein, the term "stability" refers to storage stability (e.g., room-temperature storage stability) as well as "in vivo" stability. The foregoing protecting group protects the peptides of the present invention from the attack of in vivo protein cleavage enzymes.

According to another aspect of the present invention, the present invention provides a composition for alleviating or treating hypomelanosis, containing, as an active ingredient, the foregoing peptide including one amino acid sequence selected from the group consisting of amino acid sequences of SEQ ID NO: 1 and SEQ ID NO: 2.

Since the composition of the present invention contains, as an active ingredient, the foregoing peptide including the amino acid sequence of SEQ ID NO: 1 or SEQ ID NO: 2, the descriptions of the overlapping contents therebetween will be omitted to avoid excessive complication of the present specification.

As validated in the following examples, the peptide including the amino acid sequence of SEQ ID NO: 1 or SEQ ID NO: 2 increases the expression of tyrosinase to promote melanogenesis, and thus the effective is very effective in the treatment or prevention of hypomelanosis.

The composition for alleviating or treating hypomelanosis disease can be used for all diseases caused since the melanogenesis does not arrive at the normal level due to the loss of melanocytes or the inhibition of melanogenesis, and may be used for, for example, vitiligo, albinism, nevus depigmentosus, pseudoleucoderma atopicum, Tinea versicolor, post-inflammatory depigmentation, morphea, piebaldism, Idiopathic guttate hypomelanosis, or leucoderma punctatum.

According to one embodiment of the present invention, the composition of the present invention contains: (a) a pharmaceutically effective amount of the above-described peptide of the present invention; and (b) a pharmaceutically acceptable carrier.

As used herein, the term "pharmaceutically effective amount" refers to an amount sufficient to attain efficacy or activity of the foregoing peptide.

The pharmaceutically acceptable carrier contained in the pharmaceutical composition of the present invention is usually used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and agents are described in detail in *Remington's Pharmaceutical Sciences* (19th ed., 1995).

The pharmaceutical composition of the present invention may be administered orally or parenterally, and examples of the parenteral administration may include intravenous, subcutaneous, intramuscular, intraperitoneal, local, and transdermal injections.

A suitable dose of the pharmaceutical composition of the present invention may vary depending on various factors, such as the method for formulation, manner of administration, the age, body weight, gender, and morbidity of the patient, diet, time of administration, route of administration, excretion rate, and response sensitivity. Meanwhile, the dose of the pharmaceutical composition of the present invention is 0.0001-200 μg per day.

The pharmaceutical composition of the present invention is formulated into a unit dosage form or a multidose container using a pharmaceutically acceptable carrier and/or excipient according to the method easily conducted by a person having ordinary skill in the art to which the present invention pertains. Here, the dosage form may be a solution in an oily or aqueous medium, a suspension, an emulsion, an extract, a powder, granules, a tablet, a capsule, or a gel (e.g., a hydrogel), and may further include a dispersant or a stabilizer.

According to a certain embodiment of the present invention, the composition of the present invention is a cosmetic composition containing: (a) a cosmetically effective amount of the above-described peptide of the present invention; and (b) a cosmetically acceptable carrier.

As used herein, the term "cosmetically effective amount" refers to an amount sufficient to attain efficacy or activity of the foregoing peptide.

The cosmetic composition of the present invention may be formulated into any dosage form that is conventionally prepared, and examples thereof may include a solution, a suspension, an emulsion, a paste, a gel, a cream, a lotion, a powder, a soap, a surfactant-containing cleansing, an oil, a powder foundation, an emulsion foundation, a wax foundation, and a spray, but are not limited thereto. More specifically, the cosmetic composition of the present invention may be prepared in a dosage form of emollient lotion, nourishing lotion, nourishing cream, massage cream, essence, eye cream, cleansing cream, cleansing foam, cleansing water, pack, spray, or powder.

In cases where the dosage form of the present invention is a paste, a cream, or a gel, the carrier component thereof may include animal fibers, vegetable fibers, wax, paraffin, starch, tragacanth, cellulose derivatives, polyethylene glycol, silicone, bentonite, silica, talc, and zinc oxide.

In cases where the dosage of the present invention is a powder or a spray, examples of the carrier component may include lactose, talc, silica, aluminum hydroxide, calcium silicate, or a polyamide powder. Especially, in cases where the dosage form of the present invention is a spray, the dosage form may additionally include a propellant, such as chlorofluorohydrocarbon, propane/butane, or dimethyl ether.

In cases where the dosage form of the present invention is a solution or an emulsion, the carrier component thereof may include a solvent, a solubilizer, or an emulsifier, for example water, ethanol, isopropanol, ethyl carbonate, ethyl acetate, benzyl alcohol, benzyl benzoate, propylene glycol, 1,3-butyl glycol oil, glycerol fatty esters, polyethylene glycol, or fatty acid esters of sorbitan.

In cases where the dosage form of the present invention is a suspension, examples of the carrier component may include: liquid diluents, such as water, ethanol, and propylene glycol; suspending agents, such as ethoxylated isostearyl alcohol, polyoxyethylene sorbitol ester, and polyoxyethylene sorbitan ester; microcrystalline cellulose; aluminum metahydroxide; bentonite; agar; and tragacanth.

In cases where the dosage form of the present invention is a surfactant-containing cleansing, examples of the carrier component may include aliphatic alcohol sulfate, aliphatic alcohol ether sulfate, sulfosuccinate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, plant oil, lanoline derivatives, and ethoxylated glycerol fatty acid ester.

The components contained in the cosmetic composition of the present invention include compositions that are commonly used in the cosmetic composition, in addition to the peptides, as active ingredients, and the carrier component thereof, for example, may include common aids, such as an antioxidant, a stabilizer, a solubilizer, vitamins, a pigment, and a flavor.

According to another aspect of the present invention, the present invention provides a pharmaceutical composition for treating or preventing obesity, containing, as an active ingredient, the foregoing peptide including one amino acid sequence selected from the group consisting of amino acid sequences of SEQ ID NO: 1 and SEQ ID NO: 2.

Since the composition of the present invention contains the foregoing peptide of the present invention as an active ingredient, the descriptions of the overlapping contents therebetween will be omitted to avoid excessive complication of the present specification.

As used herein, the term "obesity" refers to an excessive accumulation of body fat in the body.

As validated in the following examples, the peptide including the amino acid sequence of SEQ ID NO: 1 or SEQ ID NO: 2 of the present invention reduces the fat accumulated in cells and reduces the expression of genes (e.g., perilipin and PPARγ) involved in adipogenesis. Therefore, the composition of the present invention can effectively suppress obesity.

According to a certain embodiment, the composition of the present invention reduces the fat accumulated in cells and reduces the expressions of genes (e.g., perilipin and PPARγ) involved in adipogenesis. Therefore, the composition of the present invention is very effective in the treatment or prevention of obesity.

According to another aspect of the present invention, the present invention provides a method for alleviating or treating hypomelanosis, the method comprising administering, to a subject, the composition containing, as an active ingredient, the peptide including the amino acid sequence of SEQ ID NO: 1 or SEQ ID NO: 2.

According to another aspect of the present invention, the present invention provides a method for alleviating or treating obesity, the method comprising administering, to a subject, the composition containing, as an active ingredient, the peptide including the amino acid sequence of SEQ ID NO: 1 or SEQ ID NO: 2.

Since the method for alleviating or treating hypomelanosis and the method for preventing or treating obesity of the present invention employ the foregoing composition, the overlapping contents therebetween will be omitted to avoid excessive complication of the present specification.

Advantageous Effects

Features and advantages of the present invention are summarized as follows:

(i) The peptide including the amino acid sequence of SEQ ID NO: 1 or SEQ ID NO: 2 of the present invention exhibits melanogenesis increasing activity and adipogenesis inhibitory activity.

(ii) The peptide of the present invention increases the phosphorylation of MITF, which is a transcription factor to increase the expression of tyrosinase, and CREB, which increases the expression of MITF, thereby resultantly increasing the expression of tyrosinase, ultimately increasing melanogenesis.

(iii) The peptide of the present invention reduces the amount of fat accumulated in cells and reduces the expressions of perilipin and PPARγ involved in the adipogenesis mechanism, thereby ultimately inhibiting adipogenesis.

(iv) The present invention provides a composition for alleviating or treating hypomelanosis and a pharmaceutical composition for treating or preventing obesity.

MODE FOR CARRYING OUT THE INVENTION

Figure 1A:
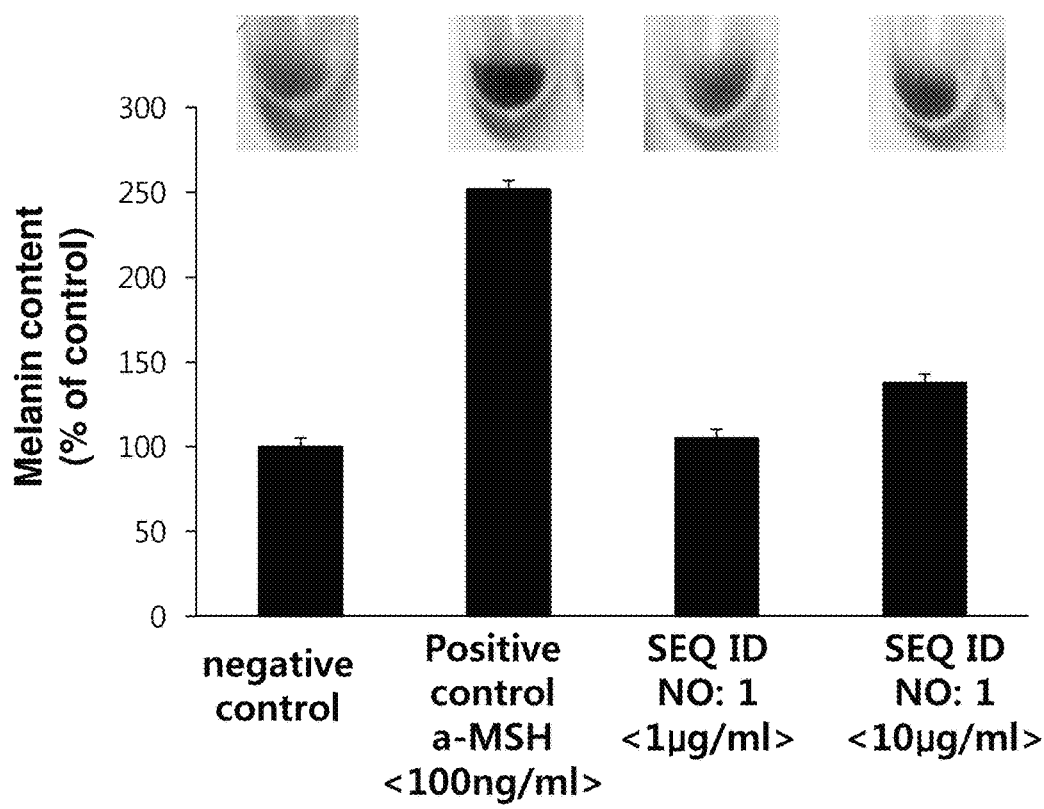
FIGS. 1a and 1b are graphs obtained by measuring the change in melanin production in melanocytes by the peptide of the present invention.

Hereinafter, the present invention will be described in detail with reference to examples. These examples are only for illustrating the present invention more specifically, and it will be apparent to those skilled in the art that the scope of the present invention is not limited by these examples.

EXAMPLES

Synthetic Example 1: Peptide Synthesis 700 mg of chloro trityl chloride resin (CTL resin, Nova Biochem Cat No. 01-64-0021) was put into a reaction vessel, and 10 ml of methylene chloride (MC) was added, followed by stirring for 3 minutes. After the solution was removed, 10 ml of dimethylform amide (DMF) was added, followed by stirring for 3 minutes, and then the solvent was again removed. 10 ml of a dichloromethane solution was put into the reaction vessel, and 200 mmole Fmoc-Cys-OH (Bachem, Swiss) and 400 mmole diisopropyl ethylamine (DIEA) were added. The mixture was well dissolved with stirring, and the reaction was conducted with stirring for 1 hour. After the reaction, the resultant material was washed, and methanol and DIEA (2:1) were dissolved in DCM, followed by reaction for 10 minutes, and then the resultant material was washed with excessive DCM/DMF (1:1). After the solution was removed, 10 ml of dimethylform amide (DMF) was added, followed by stirring for 3 minutes, and then the solvent was again removed. 10 ml of a deprotection solution (20% piperidine/DMF) was put into the reaction vessel, followed by stirring at room temperature for 10 minutes, and then the solution was removed. An equal amount of a deprotection solution was added, and then the reaction was again maintained for 10 minutes, followed by removal of the solution. The resultant material was washed twice with DMF, once with MC, and once with DMF, for 3 minutes each, thereby preparing Cys-CTL resin. 10 ml of a DMF solution was put in a new reaction vessel, and 200 mmol Fmoc-Ala (Bachem, Swiss), 200 mmol HoBt, and 200 mmole Bop were added, and the mixture was dissolved well with stirring. 400 mmole DIEA was divisionally added twice into the reaction vessel, and then the stirring was conducted for at least 5 minutes until all solids were dissolved. The dissolved amino acid mixed solution was put in the reaction vessel containing the deprotected resin, and the reaction was conducted with stirring at room temperature for 1 hour. After the reaction liquid was removed, the stirring was conducted using a DMF solution three times for 5 minutes each, followed by removal. A small amount of the reaction resin was taken to check the degree of reaction by Kaiser test (Ninhydrin test). Using the deprotection solution, the deprotection reaction was conducted twice in the same manner as described above, to prepare Ala-Cys-CTL resin. After sufficient washing with DMF and MC, the Kaiser test was again conducted, and then the following amino acid attachment test was conducted in the same manner as described above.

The chain reaction was conducted in the order of Fmoc-Ser(tBu), Fmoc-Arg(pbf), Fmoc-Phe, Fmoc-Phe, Fmoc-Arg(pbf), Fmoc-Cys(Trt), and Fmoc-Gln(Trt), on the basis of the selected amino acid sequence. The Fmoc-protecting group was removed by reaction twice with the deprotection solution for 10 min and then well washing. Acetic anhydride, DIEA, and HoBt were added to perform acetylation for 1 hour, and then the prepared peptidyl resin was washed three times with DMF, MC, and methanol, dried under the flow of nitrogen gas, and completely dried by vacuum-drying under $P_2O_5$. 30 ml of a missing solution [81.5% trifluoroacetic acid (TFA), 5% distilled water, 5% thioanisole, 5% phenol, 2.5% EDT, and 1% TIS] was added, and the reaction was maintained for 2 hours while the mixture was intermittently stirred at room temperature. The resin was filtered, washed with a small amount of a solution, and then mixed with stock solution. The distillation was conducted under reduced pressure to reduce the total volume by half, and then 50 ml of cold ether was added to induce precipitation. Thereafter, the precipitates were collected by centrifugation, followed by washing twice with cold ether. The stock solution was removed, and then sufficiently dried under nitrogen, to synthesize 0.75 g of peptide SEQ ID NO: 1, $NH_2$-Gln-Cys-Arg-Phe-Phe-Arg-Ser-Ala-Cys-COOH (yield: 86.5%). Thereafter, 0.70 g of peptide SEQ ID NO: 2, $NH_2$-Tyr-Cys-Arg-Phe-Phe-Asn-Ala-Phe-Cys-COOH was synthesized (yield: 80.7%) by the same method. According to the measurement using a molecular weight measurement instrument, the molecular weight was 1117.0 (theoretical value: 1117.3) for peptide SEQ ID NO: 1, and 1168.1 (theoretical value: 1168.3) for peptide SEQ ID NO: 2.

TABLE 1

| Peptide | Amino acid sequence | Analysis value (mass spectrometer) | |
|---|---|---|---|
| | | Analysis value | Theretical value |
| SEQ ID NO: 1 | QCRFFRSAC | 1117.0 | 1117.3 |
| SEQ ID NO: 2 | YCRFFNAFC (oxidation form) | 1168.1 | 1168.3 |

Example 1: Measurement of Melanin Production

Melanocytes (B16F10 cell line) were incubated on 6-well culture plates in an incubator at 37° C. for 24 hours, and the medium of each plate was removed, and exchanged with a new medium. Then, the cells were treated with the peptide of the present invention having the amino acid sequence of SEQ ID NO: 1 or SEQ ID NO: 2 with different concentrations. After the incubation for 72 hours, the culture medium was removed, and the cells were taken off, and then transferred into a 1.5 ml tube, followed by centrifugation at 13,000 rpm for 3 minutes. The supernatant was removed, and cell pellets were collected to measure the melanin production. 150 μl of 2 M NaOH was added to the cell pellets to dissolve intracellular melanin at 60° C. for 30 minutes. 100 μl of the supernatant, which was obtained by the dissolution, was put in each well of a 96-well plate, and the absorbance was measured at 490 nm.

Figure 1B:
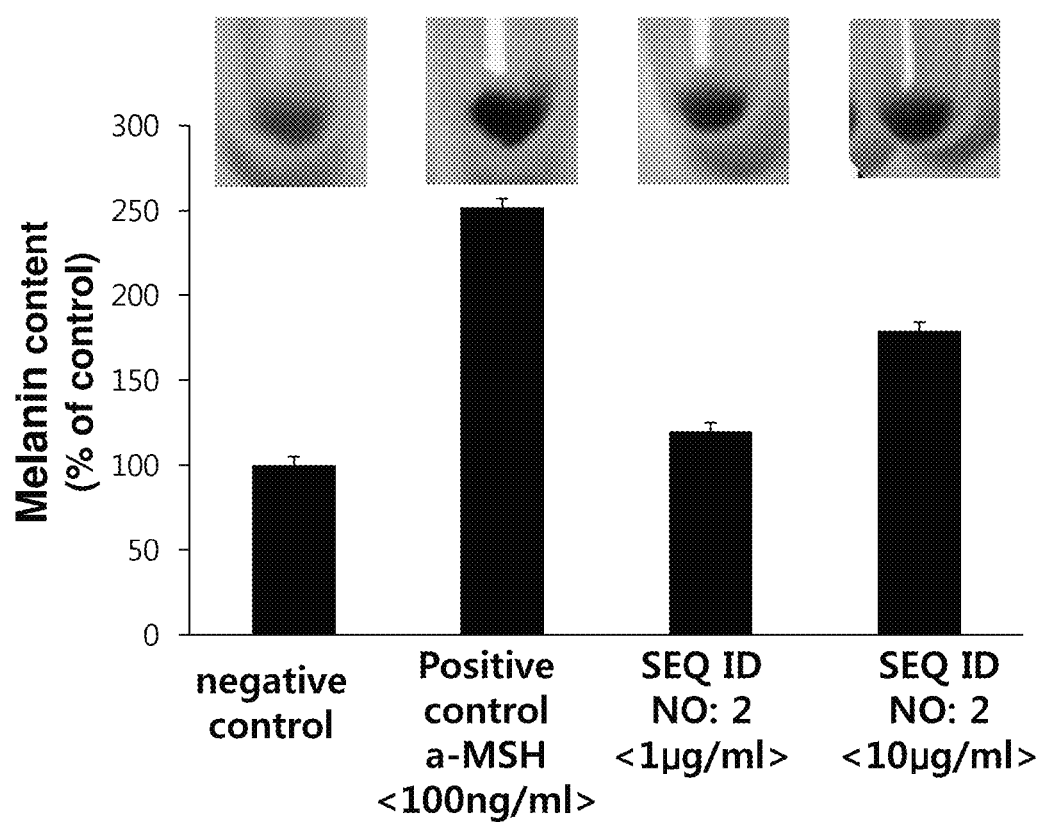

When mouse melanocytes B16F10 were treated with the peptides of the present invention with different concentrations and then incubated for 72 hours, the increase of melanogenesis in a concentration-dependent manner was observed (FIGS. 1a and 1b).

Example 2: Observation of Melanogenesis Signaling Molecules

Melanocytes (B16F10 cell line) were incubated on 6-well culture plates in an incubator for 24 hours, and were treated with the peptide of the present invention with different concentrations. After the cells were incubated for from 6 to 24 hours, the cells were dissolved, and then the CREB phosphorylation and MITF expression, which are signaling molecules involved in melanogenesis, were observed by western blot assay using antibodies specific thereto. The test was carried out using anti-pCREB antibody (Santa Cruz Biotechnology, USA) and anti-MITF antibody (Santa Cruz Biotechnology, USA).

Figure 2A:
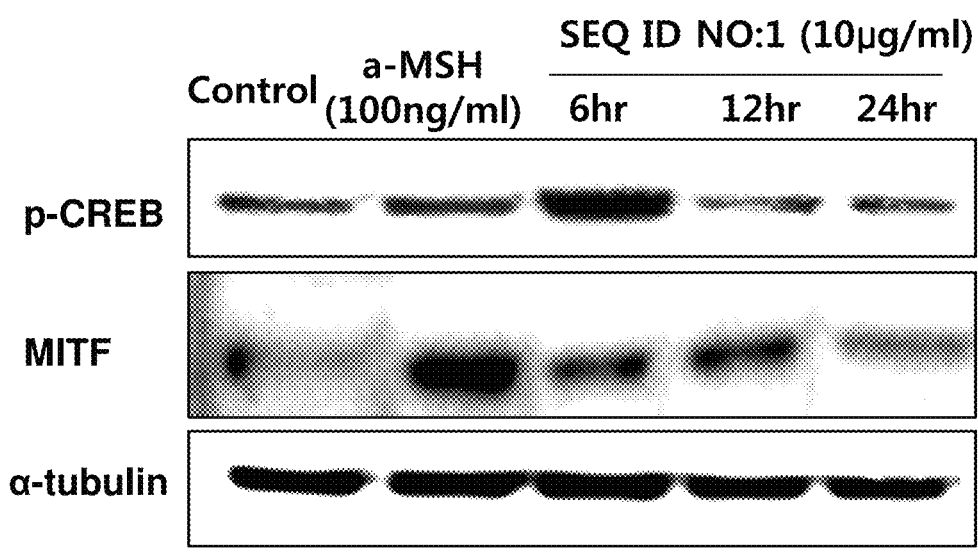
FIGS. 2a and 2b show results obtained by measuring the changes in expressions of melanogenesis signaling molecules by the peptide of the present invention through western blot assay.
Figure 2B:

When mouse melanocytes B16F10 were treated with the peptide having the amino acid sequence of SEQ ID NO: 1 or SEQ ID NO: 2, and then the changes in expressions of the melanin signaling molecules were observed over time, the phosphorylation levels of MITF, which is a transcription factor to increase the expression of a melanogenic enzyme, and CREB, which increases the expression of MITF, were increased (FIGS. 2a and 2b).

Example 3: Observation of Changes in Levels of Melanogenic Enzyme Genes

Melanocytes (B16F10 cell line) were incubated on 6-well culture plates in an incubator for 24 hours, and were treated with the peptides of the present invention with different concentrations. After the incubation for hours, the cells were taken off, and then, the increases in the expressions of tyrosinase and TRP1, which are enzymes involved in melanogenesis, were observed by RT-PCR using primers specific thereto.

Target-specific primer sequences used in PCR for enzymes involved in melanogenesis were as follows: Tyrosinase forward primer sequence, 5'-GGCCAGCTTTCAG-GCAGAGG-3' and tyrosinase reverse primer sequence, 5'-TGGTGCTTCATGGGCAAAAT-3' (annealing temperature, 51° C.); TRP1 forward primer sequence, 5'-CCGAAACACAGTGGAAGGTT-3' and TRP1 reverse primer sequence, 5'-TCTGTGAAGGTGTGCAGGAG-3' (annealing temperature, 60° C.).

Figure 3A:
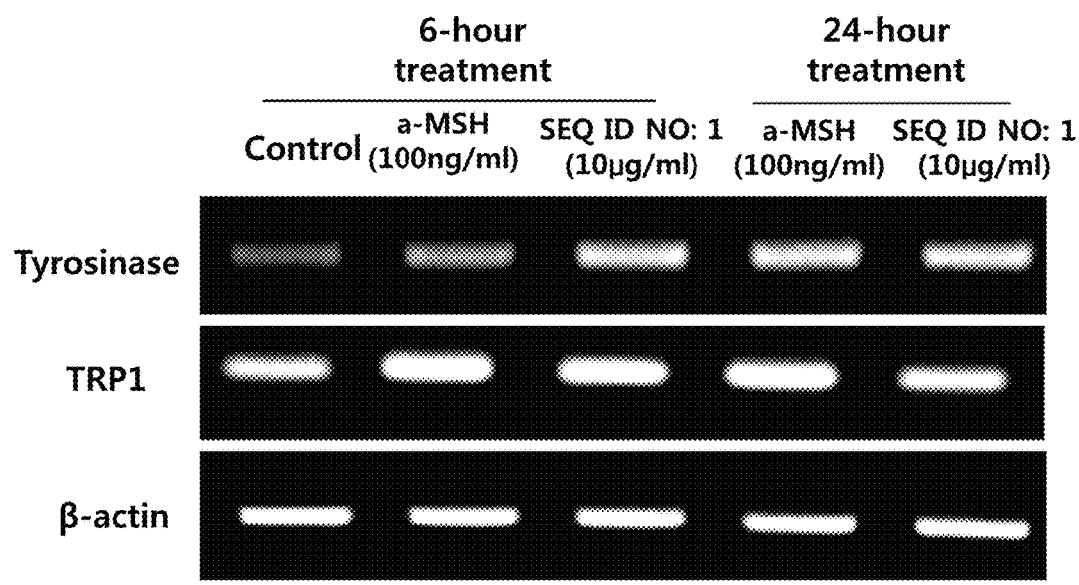
FIGS. 3a and 3b show results obtained by measuring the changes in expressions of melanogenesis signaling molecules by the peptide of the present invention through RT-PCR.
Figure 3B:
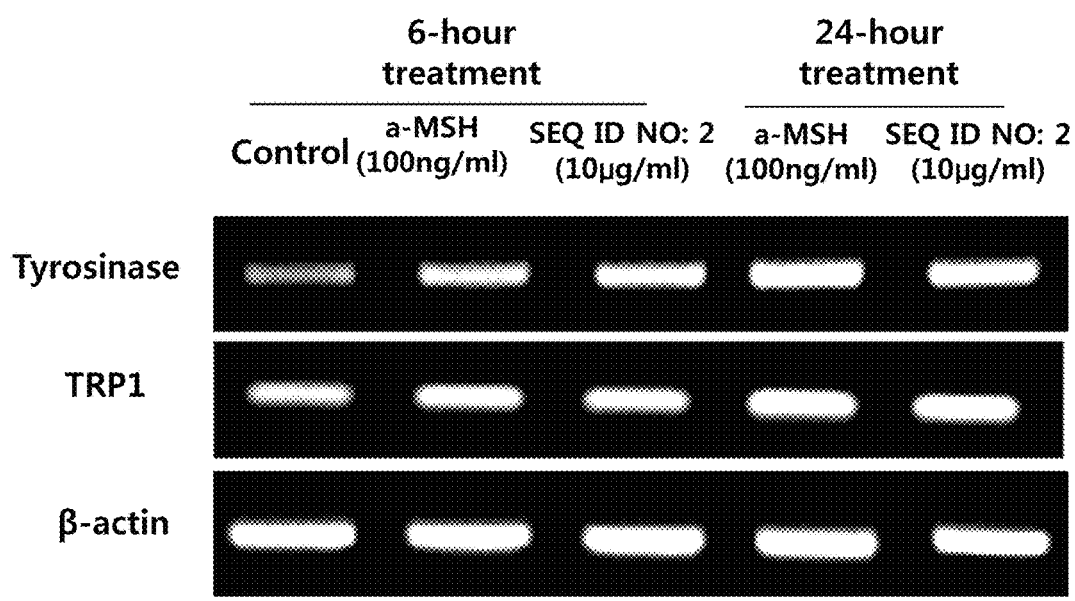

When melanocytes B16F10 were treated with the peptide having the amino acid sequence of SEQ ID NO: 1 or SEQ ID NO: 2 and the expression aspects of tyrosinase and TRP1 genes, which are enzymes involved in melanogenesis, were observed over time, it was verified that the expressions of the genes were increased compared with a control for the 6-hour treatment and 24-hour treatment (FIGS. 3a and 3b).

Example 4: Observation of Change in Level of Melanogenic Enzyme Protein

Melanocytes (B16F10 cell line) were incubated on 6-well culture plates in an incubator for 24 hours, and were treated with the peptide of the present invention with different concentrations. After the incubation for 24 hours, the cells were dissolved, and the expression of tyrosinase, which is an essential enzyme involved in melanogenesis, was observed by western blot assay using a specific antibody. The test was conducted using an anti-tyrosinase antibody (Santa Cruz Biotechnology, USA).

Figure 4A:
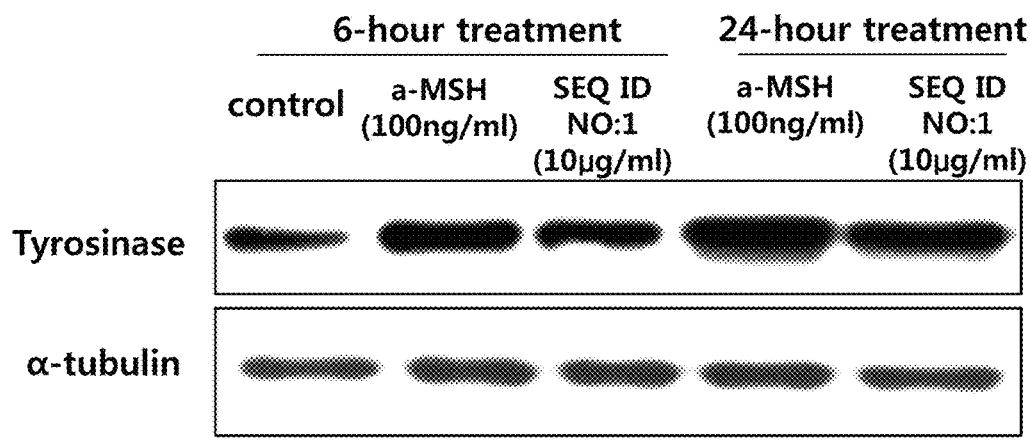
FIGS. 4a and 4b show results obtained by measuring the protein expression level of tyrosinase by the peptide of the present invention through western blot assay.
Figure 4B:
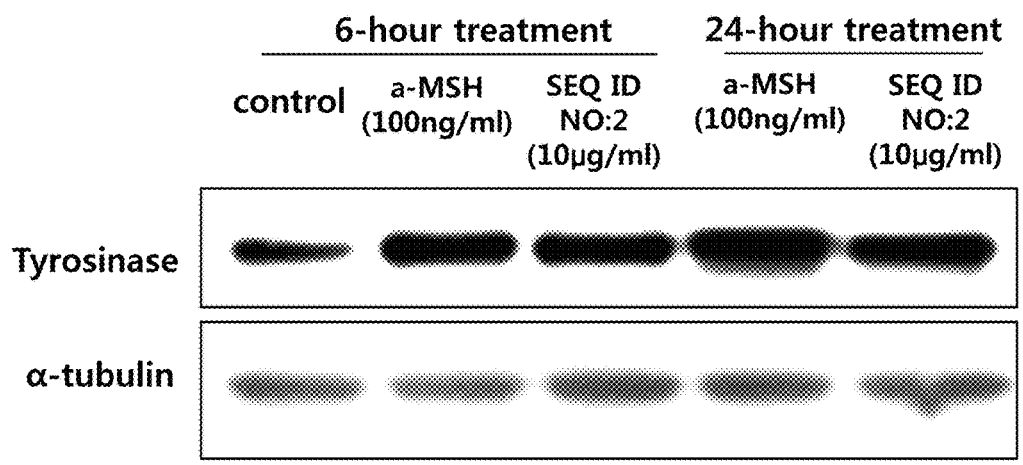

When melanocytes B16F10 were treated with the peptide having the amino acid sequence of SEQ ID NO: 1 or SEQ ID NO: 2 and the expression aspect of the tyrosinase protein involved in melanogenesis was observed over time, it was verified that the expression of the protein was increased compared with a control in view of the 6-hour treatment and 24-hour treatment (FIGS. 4a and 4b).

Example 5: Measurement of Triglyceride Amount

Pre-adipocytes (3T3-L1 cell line) were incubated on 24-well plates for 48 hours, and then treated with the peptide of the present invention with different concentrations together with a differentiation composition (0.5 mM IBMX, 0.25 mM dexamethasone, 10 mg/ml insulin), followed by incubation for 7 days.

The cells were taken off, and then put in a dissolution buffer (50 mM Tris, 150 mM NaCl, 1% Triton X-100, proteolytic enzyme inhibitor), and kept in ice for 30 minutes. After centrifugation at 14,000 g for 10 minutes, the supernatant containing an oil layer was collected, and a triglyceride reagent was added thereto, followed by reaction in an incubator at 37° C. for 5 minutes. The absorbance was measured at 540 nm to determine the amount of triglycerides.

Figure 5A:
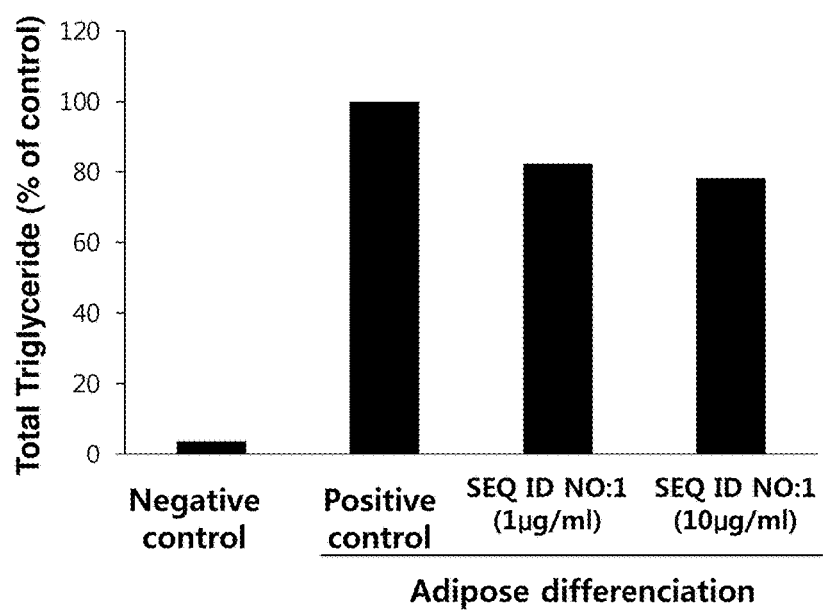
FIGS. 5a and 5b show results obtained by measuring the change in triglyceride amount in adipocytes by the peptide of the present invention.
Figure 5B:
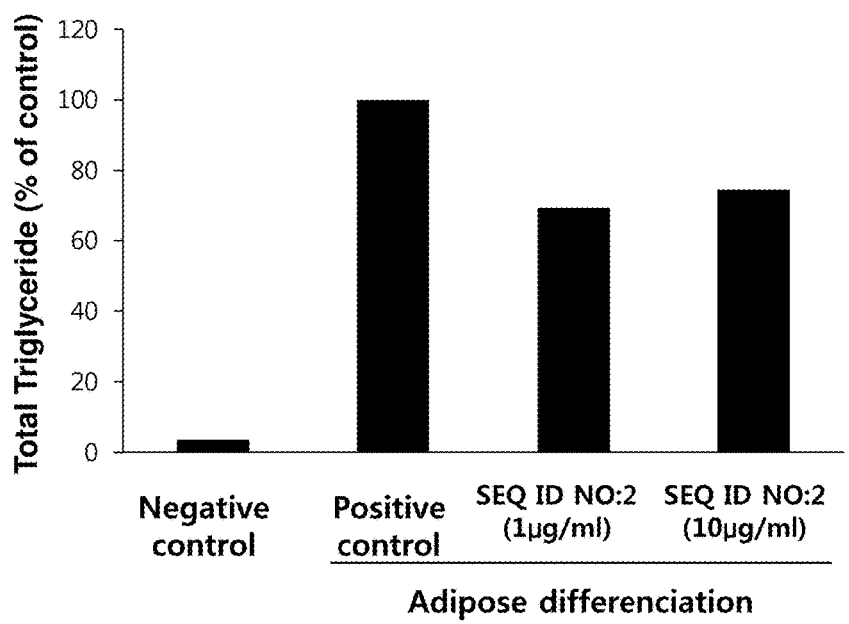

When pre-adipocytes 3T3-L1 were treated with a differentiation inducing material and the peptide having the amino acid sequence of SEQ ID NO: 1 or SEQ ID NO: 2, followed by incubation for 7 days, it was verified that, due to the inhibition of the adipogenesis mechanism, the level of triglycerides as the fat accumulated in cells was reduced in a concentration-dependent manner, compared with a control (FIGS. 5a and 5b).

Example 6: Observation of Changes of Adipogenesis-Related Genes

Pre-adipocytes (3T3-L1 cell line) were incubated on 6-well plates for 48 hours, and then treated with the present peptide with different concentrations together with a differentiation composition (0.5 mM IBMX, 0.25 mM dexamethasone, 10 mg/ml insulin), followed by incubation for 7 days. After the incubation, PT-PCR was conducted using primers specific to perilipin and PPARγ, which are genes involved in the adipogenesis mechanism. It was investigated whether the mRNA values of perilipin and PPARγ were inhibited.

Target-specific primer sequences used in PCR for enzymes involved in adipogenesis were as follows: perilipin forward primer sequence, 5'-AAGGATCCTGCACCTCA-CAC-3' and perilipin reverse primer sequence, 5'-CCTCT-GCTGAAGGGTTATCG-3' (annealing temperature, 60° C.); PPARγ forward primer sequence, 5'-TTTTCAAGGGT-GCCAGTTTC-3' and PPARγ reverse primer sequence, 5'-AATCCTTGGCCCTCTGAGAT-3' (annealing temperature, 60° C.).

Figure 6A:
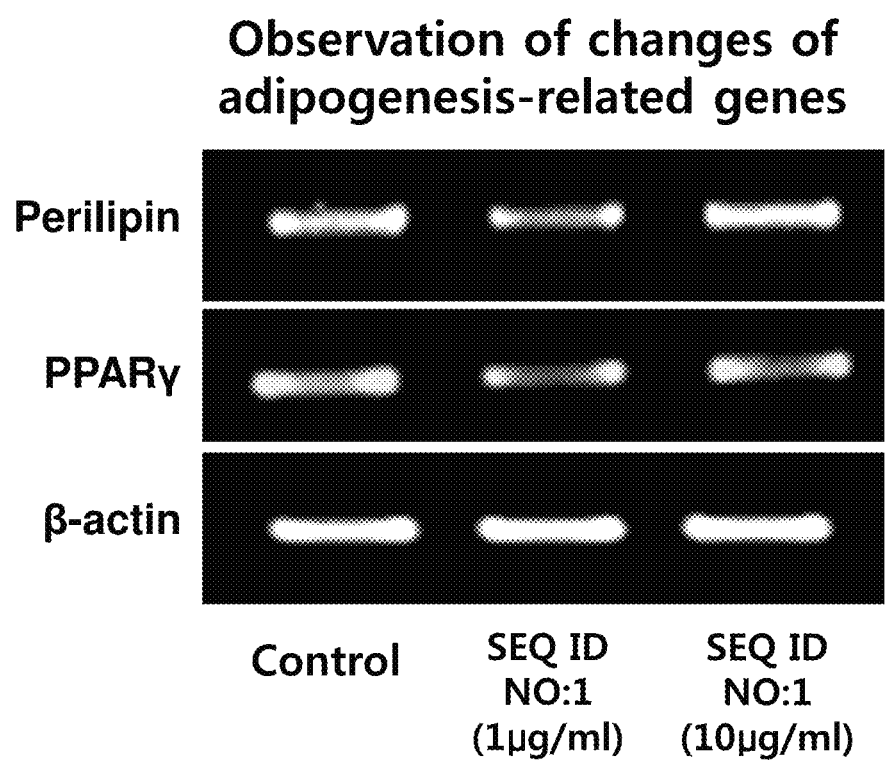
FIGS. 6a and 6b show results obtained by measuring the expressions of adipogenesis-related genes by the peptide of the present invention through RT-PCR.
Figure 6B:
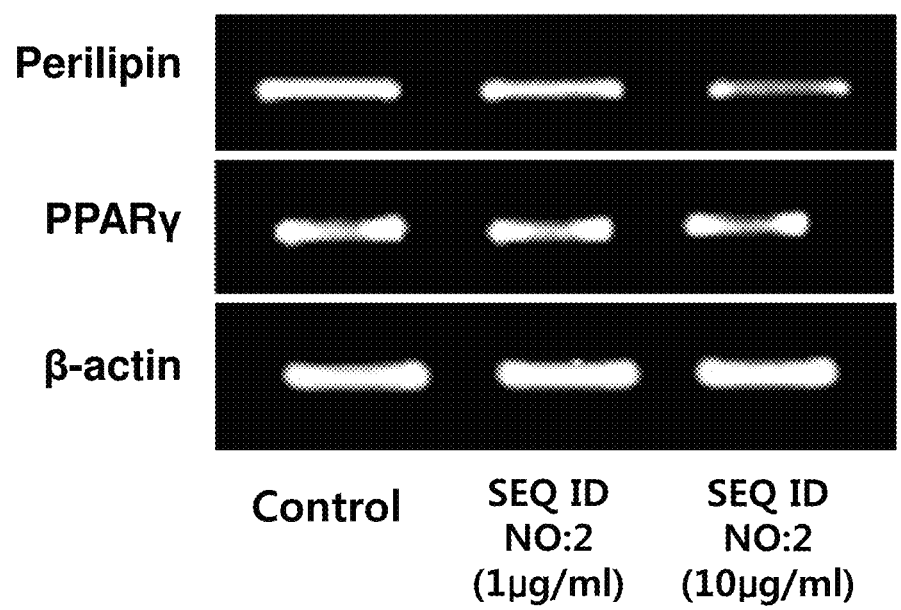

When pre-adipocytes 3T3-L1 were treated with a differentiation inducing material and the peptide having the amino acid sequence of SEQ ID NO: 1 or SEQ ID NO: 2, followed by incubation for 7 days, it was verified that the gene expressions of perilipin and PPARγ, which are molecules involved in the adipogenesis mechanism, were reduced compared with a control (FIGS. 6a and 6b).

Although the present invention has been described in detail with reference to the specific features, it will be apparent to those skilled in the art that this description is only for one embodiment and does not limit the scope of the present invention. Thus, the substantial scope of the present invention will be defined by the appended claims and equivalents thereof.

The invention claimed is:

1. A peptide having a melanogenesis increasing activity, wherein the amino acid sequence of the peptide consists of the amino acid sequence of SEQ ID NO: 1 or SEQ ID NO: 2.

2. The peptide of claim 1, wherein the peptide has activity to increase the expression of microphthalmia-associated transcription factor (MITF) and increase the phosphorylation of cAMP-responsive element binding protein (CREB).

3. The peptide of claim 1, wherein the peptide has activity to increase the expression of tyrosinase.

4. The peptide of claim 1, wherein the peptide is not modified by the presence of a protecting group.

5. A peptide having an adipogenesis inhibiting activity, wherein the amino acid sequence of the peptide consists of the amino acid sequence of SEQ ID NO: 1 or SEQ ID NO: 2.

6. The peptide of claim 5, wherein the peptide has activity to reduce the fat accumulated in cells.

7. The peptide of claim 5, wherein the peptide has activity to reduce the expression of perilipin and peroxisome proliferator-activated receptor gamma (PPARγ).

8. A peptide having a melanogenesis increasing activity, wherein the amino acid sequence of the peptide consists of the amino acid sequence of SEQ ID NO: 1 or SEQ ID NO: 2, and the N- or C-terminus of the peptide is modified by the presence of a protecting group.

9. The peptide of claim 8, wherein the protecting group is selected from the group consisting of an acetyl group, a fluorenyl methoxy carbonyl group, a formyl group, a palmitoyl group, a myristyl group, a stearyl group, and a polyethylene glycol (PEG) group.

10. A peptide having an adipogenesis inhibiting activity, wherein the amino acid sequence of the peptide consists of the amino acid sequence of SEQ ID NO: 1 or SEQ ID NO: 2, and the N- or C-terminus of the peptide is modified by the presence of a protecting group.

11. The peptide of claim 10, wherein the protecting group is selected from the group consisting of an acetyl group, a fluorenyl methoxy carbonyl group, a formyl group, a palmitoyl group, a myristyl group, a stearyl group, and a polyethylene glycol (PEG) group.

* * * * *

SEQUENCE LISTING

```
<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: Synthetic construct

<400> SEQUENCE: 1

Gln Cys Arg Phe Phe Arg Ser Ala Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic construct

<400> SEQUENCE: 2

Tyr Cys Arg Phe Phe Asn Ala Phe Cys
1               5

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
ggccagcttt caggcagagg                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
tggtgcttca tgggcaaaat                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
ccgaaacaca gtggaaggtt                                          20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
tctgtgaagg tgtgcaggag                                          20
```

```
<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
aaggatcctg cacctcacac                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
cctctgctga agggttatcg                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
ttttcaaggg tgccagtttc                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
aatccttggc cctctgagat                                               20
```